United States Patent [19]

White et al.

[11] Patent Number: 4,680,825
[45] Date of Patent: Jul. 21, 1987

[54] PRESSURE-SENSING TOOTHBRUSH HOLDER

[76] Inventors: Larry White, 111 W. Clinton, Hobbs, N. Mex. 88240; Luis Ingels, 242 S. Irwindale, Asuza, Calif. 91702

[21] Appl. No.: 774,450

[22] Filed: Sep. 10, 1985

[51] Int. Cl.⁴ ............................................. A47B 9/04
[52] U.S. Cl. .................................. 15/105; 15/167 R; 128/776; 116/202; 116/212
[58] Field of Search .................. 15/22 R, 22 C, 105, 15/167 R; 116/202, 212; 128/776, 777; 434/263

[56] References Cited

U.S. PATENT DOCUMENTS

| 2,877,477 | 3/1959 | Levin | 15/167 R X |
| 3,256,031 | 6/1966 | Fillweber | 15/22 R X |
| 3,493,991 | 2/1970 | De Bianchi | 15/167 R X |
| 4,253,212 | 3/1981 | Fujita | 15/167 R |
| 4,340,069 | 7/1982 | Yeaple | 128/776 |
| 4,450,599 | 5/1984 | Scheller et al. | 15/22 R |
| 4,476,604 | 10/1984 | White | 15/105 |

FOREIGN PATENT DOCUMENTS

| 2721352 | 11/1978 | Fed. Rep. of Germany | 15/167 R |
| 609238 | 2/1979 | Switzerland | 15/22 R |
| 2097663 | 11/1982 | United Kingdom | |

OTHER PUBLICATIONS

Allen and Nahodil, *A Transducer for Measuring the Force Exerted on Teeth by a Toothbrush During Brushing*, J. Dent. Res. Supplement to No. 5, p. 1272.

Primary Examiner—Wm. Carter Reynolds
Attorney, Agent, or Firm—Banner, Birch, McKie & Beckett

[57] ABSTRACT

A device for sensing the amount of force applied to teeth during brushing. The device consists of a single toothbrush holder in which a toothbrush is pivotally supported by means of teeth and spring rib. A metal spring is arranged to provide an adjustable resistance force against pivotal movement of the toothbrush. A conventional light pen is employed to sense and indicate the pivotal movement.

18 Claims, 8 Drawing Figures

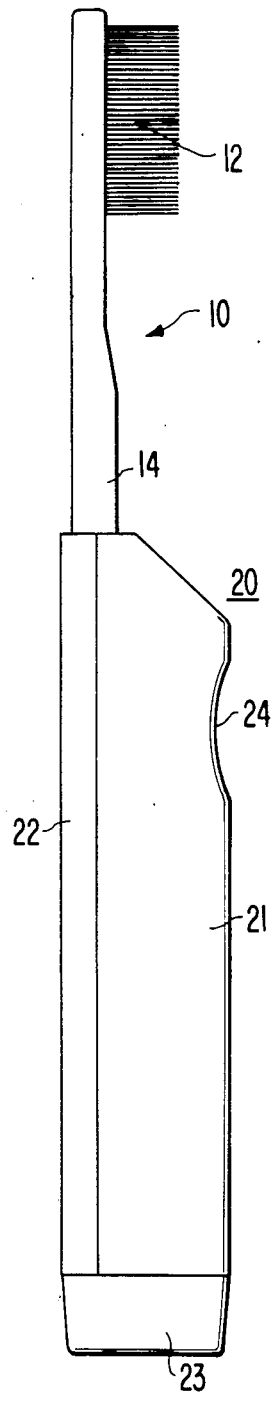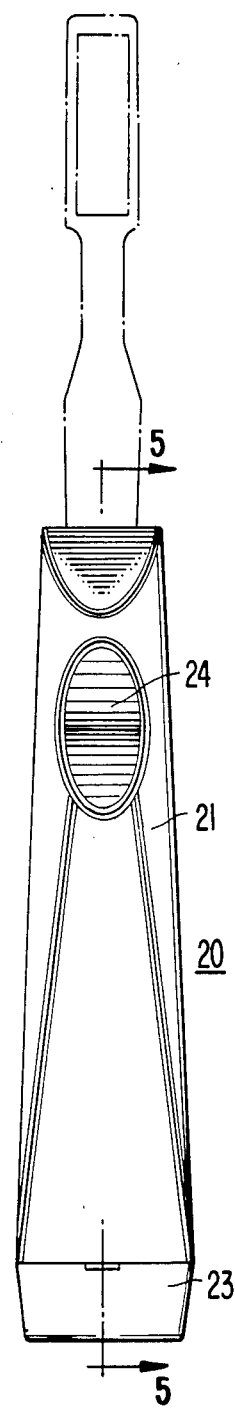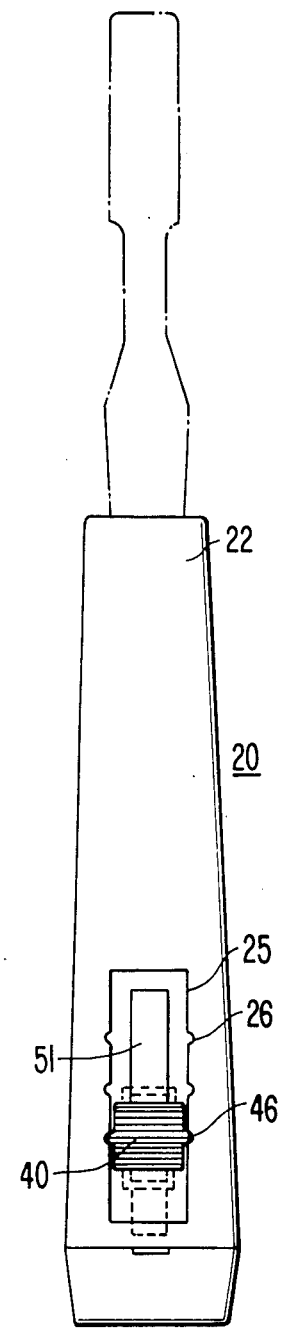

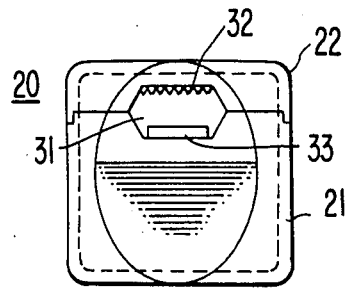
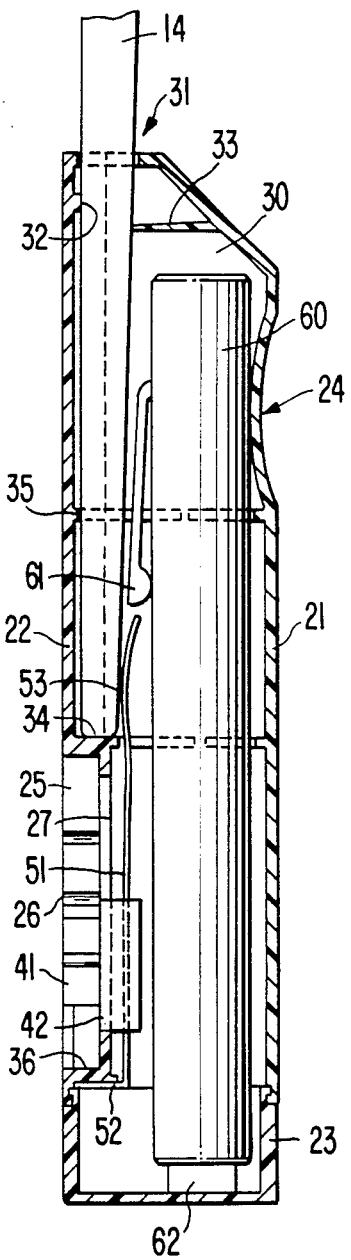
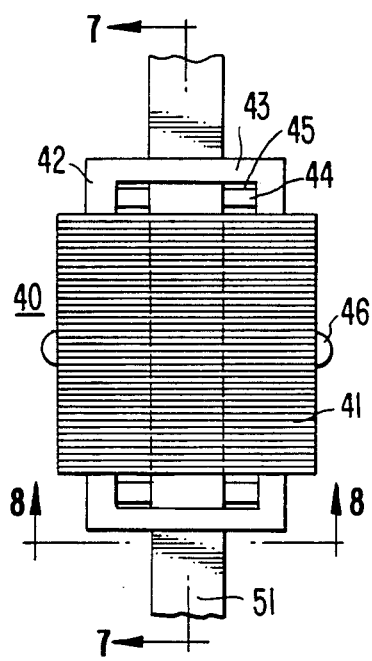
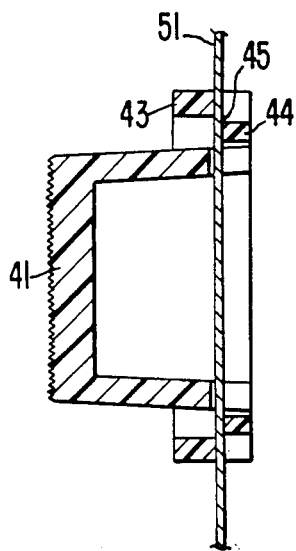
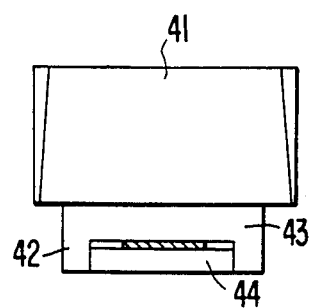

PRESSURE-SENSING TOOTHBRUSH HOLDER

TECHNICAL FIELD

The present invention relates to dental hygiene and instructional devices.

BACKGROUND OF THE INVENTION

The present invention is an improvement of the "Pressure-Sensing Device for Holding a Toothbrush" disclosed in White et al., U.S. Pat. No. 4,476,604, issued on Oct. 16, 1984.

The invention disclosed therein relates to a toothbrush holding device which indicates to the user that a preselected, but variable, amount of force is being applied to the teeth. The toothbrush holding device can be used as an instructional tool for guiding or teaching a user to gradually increase the amount of pressure applied during brushing. Further general background of the invention is described in the White et al. '604 U.S. patent incorporated herein by reference.

While the preferred embodiment disclosed in the White et al. '604 U.S. patent achieves the objective of indicating when a preselected, variable amount of force is being applied to the teeth, it has a complex structure. The embodiment includes a toothbrush holder and a sleeve in which the toothbrush holder is pivotally supported. It also employs O-rings mounted on the holder and an adjustment cap threadedly mounted on the sleeve which compress the O-rings to provide variable resistence to the pivoting of the holder. Such complex structure of the holding mechanism for the toothbrush increases manufacturing costs.

SUMMARY OF THE INVENTION

The present invention provides an improvement of a pressure-sensing toothbrush holder haivng a much simpler structure.

It is an object of the present invention to provide a pressure-sensing toothbrush holder having a single holder body, improved thus by eliminating the double body structure of a holder and a sleeve disclosed in the White et al. '604 U.S. patent.

It is an object of the present invention to provide a simple mechanism for supporting a toothbrush stem with the holder. The supporting mechanism for the toothbrush stem also works to define a pivot area about which the toothbrush can pivot with regard to the holder. This simplified mechanism serves to simplify the entire structure of the present pressure-sensing toothbrush holder.

It is also an object of the present invention to provide a simple adjustment mechanism for adjustably presetting the amount of force required to be applied to the toothbrush to activate an indicator.

It is another object of the present invention that a conventional light pen is employed as sensing and indicator mechanism so that the design and manufacturing of the present invention become very simple.

Further object of the present invention is to provide a pressure-sensing toothbrush holder which is easily handled.

In a preferred embodiment, the improved toothbrush holding device of the present invention comprises a toothbrush holder having a cavity with an opening at its one end which is adapted to receive a length of the toothbrush stem. The cavity is also adapted to store a conventional light pen which serves as an indicator. Plastic teeth are molded in the vicinity of the one opening and extend into the cavity. A plastic spring rib is also molded in the vicinity of the one opening and extends into the cavity in the opposite direction of the teeth so that the teeth in cooperation with a spring rib serve to support the stem of the toothbrush within the holder and to also define a pivot area of the toothbrush with regard to the holder. A metal spring has one end fixed to the holder in the vicinity of the opposite end of the cavity and its other end extending to the stem of the toothbrush. The metal spring is adapted to exert force to resist pivoting motion of the toothbrush within the cavity of the holder. The metal spring is adjustably fixed in the middle by a slide button which is slidably mounted on the holder so as to adjust the force exerted to the stem of the toothbrush, thereby adjusting the amount of force required to activate the indicator.

In this preferred embodiment, a conventional light pen is used to sense and indicate the pivoting motion of the toothbrush. The light pen is stored in the cavity of the holder. It has a clip which serves as a switch to turn on a light bulb during the time the clip is pushed and to turn off a light bulb when the clip is not pushed. The light pen is disposed so that the clip is located adjacent to the stem of the toothbrush and the clip is pushed by the stem when the stem is pivoted around the teeth, thus activating the light bulb.

BRIEF DESCRIPTION OF THE DRAWINGS

FIG. 1 is a side view of a toothbrush holding device in accordance with the present invention. FIG. 2 is a front view and FIG. 3 is a back view of the same.

FIG. 4 is a top view of the same toothbrush holding device without a toothbrush.

FIG. 5 is a cross-sectional view taken along line 5—5 of FIG. 2.

FIG. 6 is a plan view of a slide button with metal spring.

FIG. 7 is a cross-sectional view taken along line 7—7 of FIG. 6.

FIG. 8 is a side view of the same slide button with a cross-sectional view of the metal spring along line 8—8 of FIG. 6.

DETAILED DESCRIPTION OF THE INVENTION

As seen in FIGS. 1-3, an improved toothbrush holding device is indicated at 20. A conventional toothbrush 10, which has a stem 14 and a group of bristles 12 at one end of stem 14, is removably held within toothbrush holder 20. Toothbrush holder 20, being formed of a single body, may be assembled in manufacture from a front part 21, a back part 22 and an end part 23. End part 23 is preferrably made of semitransparent material so that the indicating light equipped within holder 20 can be seen by the user. Back part 22 has an elongated recess 25 wherein a slide button 40 is slidably mounted. Slide button 40 works to preset the amount of force required to be applied to the toothbrush to activate an indicator which will be described hereinafter.

Referring to FIGS. 4 and 5, holder 20 has a single cavity 30 with an opening 31 at the top end of holder 20. Stem 14 of the toothbrush extends through opening 31 and within cavity 30. When the device is used, toothbrush 10 is disposed with the side having bristles facing front part 21 of holder 20. Opening 31 is slightly larger than cross-sectional size of the portion of the stem 14 which opening 31 receives. Holder 20 has a projecting wall 34 which extends from cavity wall of back part 22 into cavity 30 to define a space wherein stem 14 is held. Projecting wall 34 is preferably located about half the length of toothbrush 10 away from opening 31. The terminal end of stem 14 is sustained by projecting wall 34 so that stem 14 cannot penetrate further into holder 20.

Holder 20 has teeth 32 which is preferrably molded together with back part 22 of holder 20 and extends into cavity 30 in the vicinity of opening 31. Holder 20 also has a plastic spring rib 33 which is preferrably molded together with front part 21 of holder 20 and extends into cavity 30 in the vicinity of opening 31 so as to confront with teeth 32. When stem 14 is held within holder 20, stem 14 is caught between teeth 32 and spring rib 33. As spring rib 33 exerts force to urge stem 14 against teeth 32, stem 14 is supported with regard to holder 20. Teeth 32 thus function as a friction surface against which stem 14 is urged by spring rib 33, whereby toothbrush 10 is held within holder 20 during normal brushing motion. Teeth 32 also act as a fulcrum about which toothbrush 10 pivots. When force is applied manually at the time of toothbrushing, stem 14 received in holder 20 tends to pivot toward the direction of front part 21 around teeth 32.

A metal spring 51 is disposed so that one end 52 is fixed to holder 20 and the other end 53 extends to the end portion of stem 14. In the present embodiment end 52 is fixed to a wall 36 extending into cavity 30 of holder 20. Wall 36 forms an end of a recess portion 25 of back part 22. Metal spring 51 extends in a longitudinal direction of holder 20 and reaches the position adjacent to the end portion of stem 14 in such a manner that the other end 53 of metal spring 51 exerts force to resist pivotal movement of stem 14. Accordingly, toothbrush does not pivot unless force applied thereto in the course of toothbrushing exceeds a certain level.

The effective length of metal spring 51 is adjustable by a slide button 40. The force applied to the end portion of stem 14, resisting the pivotal movement thereof, is thus adjustable.

Details of slide button 40 are shown in FIGS. 6–8. Slide button 40 comprises a handling part 41 which is slidably mounted in recess 25 of back part 22. Recess 25 has an elongated opening 27 with a width narrower than a width of handling part 41. A pair of beams 42 are attached underneath handling part 41 in the direction parallel to metal spring 51 and are connected by two pairs of bridges, i.e., upper bridges 43 and lower bridges 44. Beams 42 and bridges 43, 44 extend from each longitudinal end of handling part 41 and are arranged to fit opening 27 and slide along it together with handling part 41. Upper bridges 43 are disposed at the ends of beams 42 and lower bridges 44 are disposed at the positions slightly inner from bridges 43, each pair defining a small gap 45 between upper bridge 43 and lower bridge 44. Metal spring 51 passes through these two gaps 45 and thus held firmly. Handling part 41 has a pair of small projections 46 and correspondingly recess 25 of back part 22 has three pairs of depressions 26. Slide button 40 snugly fits recess 25 and stops at these three positions. Three positions respectively indicate the points where low, medium and high forces are applied to the stem 14 of toothbrush by metal spring. The lowest amount of force is applied to stem 14 at the lowest position of slide button 40 since spring 51 has the longest effective length at this position, while the highest amount of force is applied at the uppermost position of slide button 40 since spring 51 has the shortest effective length at this position.

Referring to FIG. 5 again, holder 20 contains a light pen 60 in cavity 30. Light pen 60 is a conventional light pen obtainable in market, and includes clip 61, light bulb 62 and batteries. Light bulb 62 is activated as clip 61 is pushed and it is activated only during the time clip 61 is pushed. It is not necessary to illustrate other portions of light pen 60 since it is conventional in design. Light pen 60 is disposed within cavity 30 so that clip 61 is placed adjacent to stem 14 of toothbrush opposite to the cavity wall of back part 22 of holder 20. When stem 14 pivots around teeth 32 due to force applied by a person brushing his/her teeth, stem 14 pushes clip 61 and thereby activates light bulb 62. Clip 61 acts as sensing means for the pivoting motion of stem 14. Light pen 60 also acts as indicator means for the pivoting motion of stem 14 as light bulb 62 is activated in response to the motion of clip 61. Light pen 60 is supported within cavity 30 by projection walls 34 and 35 extending from the cavity wall of holder 20 into cavity 30. Light bulb 62 is disposed at semitransparent end part 23 so that the user can recognize the indication.

Further, as seen in FIGS. 1, 2 and 5, holder 20 has a contour 24 in front part 21 of holder 20 for the purpose of ergonomical comfort. The user of the device thereby easily grasps it in use.

In operation, the user initially sets slide button 40 at the lowest position so that lowest brushing force will light bulb 62. The user is encouraged to set slide button at middle and then high position to increase the pivoting force necessary to light bulb 62. In this manner, the user is taught to exert increasing amounts of force when brushing, until enough force is realized.

Naturally, it should be understood that changes can be made to the disclosed preferred embodiment. Thus, it will be obvious to one of ordinary skill in the art that numerous modifications may be made without departing from the true spirit and scope of the invention, which is to be limited by the appended claims.

We claim:

1. A device for indicating that a force being applied by a toothbrush against teeth exceeds a variable, preset value, including holding means for holding a toothbrush to allow manual application of force of the toothbrush, adjustment means for adjustably presetting the amount of force required to be applied to the toothbrush to cause pivoting motion, sensing means for sensing said pivoting motion of the toothbrush when said preset amount of force is applied to said toothbrush, and indicator means for indicating when said sensing means said pivoting motion, wherein the improvement comprises:
    said holding means consisting of a single holder, said holder having a friction surface and a rib for supporting the toothbrush; and
    said adjustment means, sensing means and indicator means being included in said holder.

2. A device in accordance with claim 1 wherein said friction surface includes teeth which provide a pivot about which the toothbrush can pivot with respect to said holder.

3. A device in accordance with claim 1 wherein said friction surface is adapted to contact one side of a toothbrush stem and said rib is adapted to contact an opposite side of the toothbrush stem.

4. A device for indicating that a force being applied by a toothbrush against teeth exceeds a variable, preset value, including holding means for holding a toothbrush to allow manual application of force of the toothbrush, adjustment means for adjustably presetting the amount of force required to be applied to the toothbrush to cause pivoting motion, sensing means for sensing said pivoting motion of the toothbrush when said preset amount of force is applied to said toothbrush, and indicator means for indicating when said sensing means said pivoting motion, wherein the improvement comprises:

said holding means consisting of a single holder; and said adjustment means, sensing means and indicator means being included in said holder and said adjustment means including a metal spring.

5. A device in accordance with claim 4 wherein the force of said metal spring is adjustable by a slide button carried by said holder.

6. A device for indicating that a force being applied by a toothbrush against teeth exceeds a variable, preset value, including holding means for holding a toothbrush to allow manual application of force of the toothbrush, adjustment means for adjustably presetting the amount of force required to be applied to the toothbrush to cause pivoting motion, sensing means for sensing said pivoting motion of the toothbrush when said preset amount of force is applied to said toothbrush, and indicator means for indicating when said sensing means said pivoting motion, wherein the improvement comprises:

said holding means consisting of a single holder; and said adjustment means, sensing means and indicator means being included in said holder, said sensing means and said indicator means comprising a light pen.

7. A device in accordance with claim 6 wherein pivotal motion of a stem of a toothbrush directly activates said light pen by pushing a clip of said light pen.

8. A device in accordance with claim 6 wherein said holder has a contour for easy handling.

9. A device for indicating that a predetermined force is being applied against teeth by a toothbrush having an elongated stem and a group of bristles attached to a portion of the stem, comprising:

a toothbrush holder having a cavity adapted to receive a length of the toothbrush stem and means for fixing the stem in said cavity;

pivot means inside the cavity of said holder acting as a fulcrum about which said toothbrush pivots;

said means for fixing the stem including a friction surface and a spring rib and said friction also serves as said pivot means;

adjustable resistance means for variably resisting the pivoting of said toothbrush inside said holder;

sensing means located in said holder for sensing the pivoting of said toothbrush; and indicating means located in said holder for indicating when said sensing means senses the pivoting of said toothbrush.

10. A device in accordance with claim 9 wherein said friction surface includes teeth for contacting one side of the toothbrush stem and said spring rib is adapted for contacting the other side of the toothbrush stem.

11. A device for indicating that a predetermined force is being applied against teeth by a toothbrush having an elongated stem and a group of bristles attached to a portion of the stem, comprising:

a toothbrush holder having a cavity adapted to receive a length of the toothbrush stem and means for fixing the stem in said cavity;

pivot means inside the cavity of said holder acting as a fulcrum about which said toothbrush pivots;

adjustable resistance means for variably resisting the pivoting of said toothbrush inside said holder, said adjustable resistance means includig a metal spring and a slide button;

sensing means located in said holder for sensing the pivoting of said toothbrush; and indicating means located in said holder for indicating when said sensing means senses the pivoting of said toothbrush.

12. A device for indicating that a predetermined force is being applied against teeth by a toothbrush having an elongated stem and a group of bristles attached to a portion of the stem, comprising:

a toothbrush holder having a cavity adapted to receive a length of the toothbrush stem and means for fixing the stem in said cavity;

pivot means inside the cavity of said holder acting as a fulcrum about which said toothbrush pivots;

adjustable resistance means for variably resisting the pivoting of said toothbrush inside said holder;

sensing means located in said holder for sensing the pivoting of said toothbrush; and indicating means located in said holder for indicating when said sensing means senses the pivoting of said toothbrush, said sensing means and said indicating means comprising a light pen.

13. A device in accordance with claim 12 wherein a switching means of said light pen is disposed for directly sensing the pivoting motion of the stem of the toothbrush.

14. A device in accordance with claim 12 wherein said toothbrush holder has a contour for easy handling.

15. A device for indicating that a predetermined force is being applied against teeth by a toothbrush having an elongated stem and a group of bristles attached to a portion of the stem comprising:

a toothbrush holder having a cavity with an opening at one end of the holder, said cavity being adapted to receive a length of the toothbrush stem;

a pivot rib fixed to the holder in the vicinity of said opening and extending into said cavity;

a spring rib extending from the holder into said cavity in the direction opposite to said pivot rib in the vicinity of said opening and supporting the stem of the toothbrush in cooperation with said pivot rib;

a metal spring having one end fixed to the holder in the vicinity of the opposite end of the opening of the cavity, extending to the end portion of the stem of the toothbrush for exerting force to resist the pivotal movement of the stem of the toothbrush;

a slide button slidably mounted on the holder and adjustably fixing said metal spring in the middle to adjust the force exerted by said metal spring on the stem of the toothbrush; and a light pen in the cavity of the holder, having a clip which serves as a switch to activate a light bulb when the clip is pushed, said clip being disposed adjacent to the stem of the toothbrush so that the clip is pushed by the pivotal movement of the stem.

16. A device in accordance with claim 15 wherein said toothbrush holder has a contour for easy handling.

17. A device in accordance with claim 15 wherein said slide button includes a handling part slidably received in a longitudinal recess in said holder and means for slidably coupling said metal spring to said slide button.

18. A device in accordance with claim 17 wherein said coupling means includes upper and lower bridges at either end of said slide button through which said metal spring passes.

* * * * *

UNITED STATES PATENT AND TRADEMARK OFFICE
CERTIFICATE OF CORRECTION

PATENT NO. : 4,680,825
DATED : July 21, 1987
INVENTOR(S) : Larry White and Luis Ingels It is certified that error appears in the above-identified patent and that said Letters Patent is hereby corrected as shown below:

Claim 4, Column 5, line 8, after "said sensing means" insert —senses—; and

Claim 6, Column 5, line 26, after "said sensing means" insert —senses—.

Signed and Sealed this

Eighth Day of December, 1987

Attest:

DONALD J. QUIGG

*Attesting Officer*          *Commissioner of Patents and Trademarks*